United States Patent
Khavinson et al.

(10) Patent No.: US 7,625,870 B2
(45) Date of Patent: Dec. 1, 2009

(54) PEPTIDE SUBSTANCE RESTORING RESPIRATORY ORGANS FUNCTION

(75) Inventors: Vladimir Khatskelevich Khavinson, St. Petersburg (RU); Galina Anatolievna Ryzhak, St. Petersburg (RU); Evgeny Iosifovich Grigoriev, St. Petersburg (RU); Irina Yurievna Ryadnova, St. Petersburg (RU)

(73) Assignee: "Access Bioscience" CJSC, Saint-Petersburg (RU)

( * ) Notice: Subject to any disclaimer, the term of this patent is extended or adjusted under 35 U.S.C. 154(b) by 594 days.

(21) Appl. No.: 11/570,485

(22) PCT Filed: Dec. 7, 2004

(86) PCT No.: PCT/RU2004/000494

§ 371 (c)(1),
(2), (4) Date: Dec. 12, 2006

(87) PCT Pub. No.: WO2006/001729

PCT Pub. Date: Jan. 5, 2006

(65) Prior Publication Data

US 2008/0274982 A1 Nov. 6, 2008

(30) Foreign Application Priority Data

Jun. 22, 2004 (RU) ............................ 2004118700

(51) Int. Cl.
*A61K 38/07* (2006.01)
*C07K 5/04* (2006.01)

(52) U.S. Cl. .......................... 514/18; 530/330

(58) Field of Classification Search ............... None
See application file for complete search history.

(56) References Cited

U.S. PATENT DOCUMENTS 6,727,227 B1   4/2004   Khavinson

FOREIGN PATENT DOCUMENTS

RU   1681426 A1   8/1989
RU   1681427 C    11/1994

OTHER PUBLICATIONS

Ambroxol—*Register of Pharmaceutical Substances of Russia, Drug Encyclopedia*, Moscow, 2003, p. 80.
Biseptol—*Register of Pharmaceutical Substances of Russia, Drug Encyclopedia*, Moscow, 2003, p. 147.
Brifeseptol—*Register of Pharmaceutical Substances of Russia, Drug Encyclopedia*, Moscow, 2003, p. 160.
Bromhexine—*Register of Pharmaceutical Substances of Russia, Drug Encyclopedia*, Moscow, 2003, p. 161.
Butamirate—*Register of Pharmaceutical Substances of Russia, Drug Encyclopedia*, Moscow, 2003, p. 170.
Codeine—*Register of Pharmaceutical Substances of Russia, Drug Encyclopedia*, Moscow, 2003, p. 413.
Fenoterol—*Register of Pharmaceutical Substances of Russia, Drug Encyclopedia*, Moscow, 2003, p. 872.
Glaucine—*Register of Pharmaceutical Substances of Russia, Drug Encyclopedia*, Moscow, 2003, p. 232.
Ipratropium bromide—*Register of Pharmaceutical Substances of Russia, Drug Encyclopedia*, Moscow, 2003, p. 352.
Naphazoline—*Register of Pharmaceutical Substances of Russia, Drug Encyclopedia*, Moscow, 2003, p. 567.
Phtizoethamum—*Register of Pharmaceutical Substances of Russia, Drug Encyclopedia*, Moscow, 2003, p. 907.
Prenoxdiazine—*Register of Pharmaceutical Substances of Russia, Drug Encyclopedia*, Moscow, 2003, p. 688.
Rimantadine—*Register of Pharmaceutical Substances of Russia, Drug Encyclopedia*, Moscow, 2003, p. 729.
Salbutamol—*Register of Pharmaceutical Substances of Russia, Drug Encyclopedia*, Moscow, 2003, p. 742.
Secretolytics and stimulators of motor functions of respiratory ways—*Register of Pharmaceutical Substances of Russia, Drug Encyclopedia*, Moscow, 2003, pp. 1079-1080.
Theophylline—*Register of Pharmaceutical Substances of Russia, Drug Encyclopedia*, Moscow, 2003, p. 803.
Xylometazoline—*Register of Pharmaceutical Substances of Russia, Drug Encyclopedia*, Moscow, 2003, p. 434.
International Searching Authority, International Search Report and Written Opinion for International Application No. PCT/RU2004/000494 dated Apr. 20, 2005.
Khavinson, V. Kh. And Malinin, V. V.: "Mechanisms underlaying geroprotective effects of peptides," Bulletin of Exprimanetal Biology and Medicine, vol. 133, No. 1, Jan. 2002, pp. 1-5, XP002324988.

*Primary Examiner*—Andrew D Kosar
(74) *Attorney, Agent, or Firm*—Leydig, Voit & Mayer, Ltd.

(57) ABSTRACT

The invention refers to the medicinal remedies for respiratory system diseases treatment and may be applied as a substance, capable of restoring respiratory organs functions and used for treatment of different forms of lung pathology. There is proposed a biologically active new tetrapeptide alanyl-glutamyl-aspartyl-leucine of the general formula Ala-Glu-Asp-Leu, capable of restoring respiratory organs function. There is proposed a pharmaceutical substance, containing as an active peptide agent an effective amount of tetrapeptide alanyl-glutamyl-aspartyl-leucine of the general formula Ala-Glu-Asp-Leu, which if used in the medical preparation contributes to the restoration of the respiratory organs function.

8 Claims, No Drawings

PEPTIDE SUBSTANCE RESTORING RESPIRATORY ORGANS FUNCTION

The invention refers to the remedies for respiratory system disease treatment and may be applied as a substance, capable of restoring respiratory organs functions and used for treatment of different forms of lung pathology.

Nowadays there is observed a growing tendency towards increased incidence of respiratory organs diseases. In particular, non-specific lung diseases ranks. $3^{rd}$ after cardiovascular diseases and malignant tumors regarding their significance among general morbidity and mortality. That is why the invention of new medicinal substances, which may be employed in treatment for respiratory system diseases, becomes of great social importance, especially for infectious respiratory diseases, bronchitis, emphysema, bronchial asthma. The symptoms of these diseases are cough, sputum discharge, dyspnea. That is why treatment and prevention of the respiratory system diseases consist of several complex measures. These are: impact on causative agent in case of infectious (bacterial or/and viral) disease and symptomatic treatment with antitussive, expectorant and broncholitic preparations, and also immunocorrective and mucolitic therapy.

Among therapeutic measures of infectious diseases treatment there should be enumerated sulfanilamide preparations combined with other antibacterial drugs, such as Biseptol, Brifeseptol, Phtizoethamum (Register of Pharmaceutical Substances of Russia. Drug Encyclopedia.—Moscow, 2003.—147p, 160p, 907p), fluorine chinon group antibiotics and antiviral pharmaceuticals, such as Rimantadine (Register of Pharmaceutical Substances of Russia. Drug Encyclopedia.—Moscow, 2003.—729p). Among pharmaceuticals, which are used for symptomatic treatment, there should be mentioned drugs, capable of diminishing bronchi mucous membranes edema, such as Xylometazoline, Naphazoline (Register of Pharmaceutical Substances of Russia. Drug Encyclopedia.—Moscow, 2003.—434p, 567p), antitussive preparations: Codeine, Butamirate, Glaucin, Prenocdiasin (Register of Pharmaceutical Substances of Russia. Drug Encyclopedia.—Moscow, 2003.—413p, 170p, 232p, 688p), and also mucolitic preparations. The latter are used to dilute sputum in case of obstructive bronchitis, pneumonia, broncholiolitis, bronchial asthma, atelectasises, bronchial obstruction. They are also quite often employed for prevention of complications after surgery on respiratory organs. This group includes such ferments as: Trypsinum, Chimotrypsinum, Ribonucleasum and compounds, containing sulphur (Acetylcysteine, Carbocisteine) (Register of Pharmaceutical Substances of Russia. Drug Encyclopedia.—Moscow, 2003.—1079p), derivatives of Visizine alkaloid: Bromhexin, Ambroxol (Register of Pharmaceutical Substances of Russia. Drug Encyclopedia.—Moscow, 2003.—161p, 80p). The most widely used are those, containing sulphur and Visizine derivatives. Preparations containing sulphur are especially effective in case of bronchitis and other diseases, accompanied by laboured expectoration. As expectorant remedies eliminate only one symptom of the disease, that is cough with laboured sputum discharging, they are usually used together with other preparations, such as: antibacterial and antiviral, antipyretic, antiedemal, immune-stimulators, vitamins (Register of Pharmaceutical Substances of Russia. Drug Encyclopedia.—Moscow, 2003.—1079p).

Patients suffering obstructive bronchitis (bronchitis accompanied by bronchi spasm) report better effect when the combination of substances, capable of dilating bronchi, and those, capable of sputum diluting is used. As bronchodilating substances there are employed such preparations as Fenoterol, Salbutamol (Register of Pharmaceutical Substances of Russia. Drug Encyclopedia.—Moscow, 2003.—872p, 742p), capable of stimulating adenoreceptors. Moreover they possess antiedematic effect. M-cholinoblockators (ipratropium bromide) debilitate bronchi smooth muscles and bronchi spasm (Register of Pharmaceutical Substances of Russia. Drug Encyclopedia.—Moscow, 2003.—352p). Xanthine theotard derivative (Register of Pharmaceutical Substances of Russia. Drug Encyclopedia.—Moscow, 2003.—802p) reveals antiasthmatic, broncholitic, vasodilative and miorelaxating effect. All the stated above preparations reduce mucus, which is discharged by fibrillar epithelium of bronchi, impair inflammation and edema of mucous membrane, ease sputum discharging.

But often, medicamentous treatment does not lead to positive results, as it is conducted with a help of preparations, aimed at elimination of either a cause of disease, or its symptoms. But the majority of preparations do not produce specific effect on functional state of lungs and bronchi, at the same time they reveal side effects and contra-indications. Thus, a lot of above mentioned preparations negatively affect gastrointestinal tract, they are contra-indicated to patients suffering hepatic insufficiency, myocardial infarction, arrhythmia and epilepsy. In many cases their administration leads to the development of allergic reactions, nausea, vomiting, pains in epigastric region.

It should be noticed, that nowadays there are objectively no preparations capable of restoring lung tissue and bronchi mucous membrane functions after the development of pathologic process, irrespective of the reasons, which triggered it.

There is known a preparation of polypeptide nature (RF patent No 1681427 <<Method of obtaining the substance, capable of increasing the lung antibacterial resistance>>, 1989, ICI A 61K 35/24), isolated from organic materials (animal lungs). Employment of this preparation in medical practice is limited due to complicated method of its obtaining, small output of active agents, high variability of its chemical and physical properties and due to possible allergic reactions, which can be revealed by the patients.

There is known a preparation of polypeptide nature (RF patent No 1681426 "Method of obtaining the substance, capable of restoring lung respiratory function, 1989, ICI A 61K 35/24), isolated from organic materials (animal tracheae), possessing analogous biological activity and being the closest analogue, taken as a prototype for pharmacologic substance (pharmaceutical composition).

Employment of this preparation in medical practice is limited due to complicated method of obtaining, small output of active agents, high variability of its chemical and physical properties and also due to possible allergic reactions, which can be revealed by the patients.

It should be noticed that the proposed peptide compound is a tetrapeptide having no structural analogues.

The proposed invention is designed to obtain a new biologically active compound of peptide nature restoring function of respiratory organs, Technical result of the invention is a design of a new peptide compound and pharmacological substance (pharmaceutical composition), containing this peptide compound as an active agent, capable of restoring respiratory organs function.

The possibility of obtaining technical result using this invention is confirmed by the reliable data, represented by the examples and results of the experiments, attained according to the following methods accepted in this field.

The present invention describes a new tetrapeptide alanyl-glutamyl-aspartyl-leucine of the general formula Ala-Glu-Asp-Leu of sequence 1 [SEQ ID NO: 1].

The tetrapeptide is obtained by a classical method of peptide synthesis in a solution (Yakubke Kh.-D., Eshkeit Kh. Amino acids, peptides, proteins: Translated from German.—Mir, Moscow.—1985.—456 pp.).

The present invention describes tetrapeptide alanyl-glutamyl-aspartyl-leucine of the general formula Ala-Glu-Asp-Leu of sequence 1 [SEQ ID NO: 1] revealing biological activity, and namely, restoring function of respiratory organs.

The restorative effect of Ala-Glu-Asp-Leu (SEQ ID NO:1) tetrapeptide on respiratory organs has been revealed experimentally in induced pathology, and namely using such models as:

acute pneumonia caused by bacterial injury of rats;
chronic fibrosing inflammatory process (lung bleomycine fibrosis in rats);
sublethal hyperoxic lung injury in rats;
study of the growth of pubertal rats lung organotypical culture explantats.

It is known that all the above described pathologies are characterized by pronounced disorders of lung morphology, particular for each of the studied pathologies. Thus, in case of acute bacterial lung injury t his manifests in pronounced inflammatory reaction, exudation of alveolae into the lumen, infiltration of the interalveolar septa by neutrophile leukocytes, edema of perivascular and peribronchial areas. In case of lingering inflammatory process in lungs (sublethal hyperoxic injury, bleomycine fibrosis), irrespective of disease etiology, there was registered a significant disorder in morphology of lung respiratory regions, accompanied by emphysema and fibrosis with foci of inflammation. These changes were registered together with a development of hemodynamic changes in the pulmonary blood circulation, compensatory myocardial hypertrophy, delay of body weight increase in experimental animals. The pathologies under review, irrespective of the reasons that caused them, are associated with a significant change of the broncho-alveolar lavage fluid (BALF) cellular content, towards the increase in the number of neutrophiles and less pronounced increase in the number of lymphocytes, meanwhile relative number of alveolar macrophages (AM) significantly decreases. AM are known to be active polyfunctional cells, which competence determines state of the non-specific resistance system, regulation of humoral and cellular immune response on the level of lungs and organism in general, and also processes of reparation. In case of pathology process development there take place oppression of AM phagocytic activity and hyperactivation of oxidation processes in BALF cells, which contributes to the development of disorders of respiratory organs inner structure and functions.

The tetrapeptide Ala-Glu-Asp-Leu (SEQ ID NO:1) was experimentally proved to be non-toxic.

The present invention also refers to the pharmacological substance (pharmaceutical composition), restoring the function of respiratory organs, containing as its active peptide agent an effective amount of the tetrapeptide alanyl-glutamyl-aspartyl-leucine of the general formula Ala-Glu-Asp-Leu of the sequence 1[SEQ ID NO: 1].

The notion "pharmaceutical substance" under this application implies the use of a drug form containing the effective amount of the tetrapeptide of the general formula Ala-Glu-Asp-Leu, which can find its preventive and/or therapeutic employment in medicine as a substance restoring the function of the respiratory organs.

The notion "therapeutically effective amount" under this application implies the use of such amount of the active peptide agent, which, in compliance with the quantitative indices of its activity and toxicity, as well as with respect to the special knowledge available, shall be effective in this drug form.

To obtain pharmaceutical composition meeting the invention, the proposed tetrapeptide is blended as an active ingredient with a pharmaceutical carrier in accordance with the methods of compounding accepted in pharmaceutics.

The carrier may have various forms depending on the drug form of the substance desirable for introduction into a body, for example parenteral or oral administration.

To produce drug composition for oral administration there can be used all known pharmaceutical components.

The carrier for parenteral administration usually includes sterile 0.9% NaCl solution or sterile water, though there could be employed other ingredients instrumental for stability or maintaining sterility.

The invention is illustrated by the tables:

Table 1 demonstrates the effect of the tetrapeptide Ala-Glu-Asp-Leu (SEQ ID NO:1) on dynamics of BALF cytogram in rats in case of acute bacterial lung injury.

Table 2 demonstrates the effect of the tetrapeptide Ala-Glu-Asp-Leu (SEQ ID NO:1) on dynamics of alveolar macrophages' phagocytic activity in rats in case of acute bacterial lung injury.

Table 3 demonstrates the effect of the tetrapeptide Ala-Glu-Asp-Leu (SEQ ID NO:1) on biometrical indices of rats exposed to thrice-repeated intratracheal administration of bleomycine.

Table 4 demonstrates the effect of the tetrapeptide Ala-Glu-Asp-Leu (SEQ ID NO:1) on the content of immune complexes in the blood serum and BALF of rats in case of acute bacterial lung injury, exposed to thrice-repeated intratracheal administration of bleomycine.

Table 5 demonstrates the effect of the tetrapeptide Ala-Glu-Asp-Leu (SEQ ID NO:1) on the dynamics of biometrical indices of rats exposed to sublethal hyperoxic lung injury.

Table 6 demonstrates the effect of the tetrapeptide Ala-Glu-Asp-Leu (SEQ ID NO:1) on the indices of BALF cytogram and alveolar macrophages's phagocytic activity exposed to sublethal hyperoxic lung injury.

Table 7 demonstrates the effect of the tetrapeptide Ala-Glu-Asp-Leu (SEQ ID NO:1) on the growth of rat lung tissue organotypical explants.

Table 8 demonstrates the effect of the tetrapeptide on morphologic and biochemical indices of peripheral blood of guinea pigs.

The proposed invention is illustrated by the example of the tetrapeptide Ala-Glu-Asp-Leu (SEQ ID NO:1) synthesis (Example 1), by the examples of the tetrapeptide biological activity (examples 2, 3, 4, 5), by the example of testing the tetrapeptide for toxicity (example 6), demonstrating its pharmacological properties and confirming the possibility of attaining a therapeutically effective pharmaceutical composition.

EXAMPLE 1

Synthesis of Ala-Glu-Asp-Leu (SEQ ID NO:1) tetrapeptide

1. Product name: L-alanyl-L-glutamyl-L-aspartyl-L-leucine
2. Structural formula:

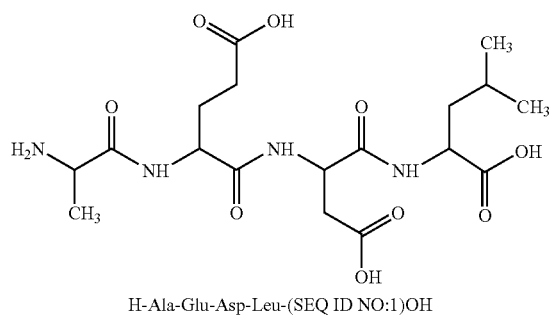

H-Ala-Glu-Asp-Leu-(SEQ ID NO:1)OH

3. Molecular formula without ion pair: $C_{18}H_{30}N_4O_9$
4. Molecular weight without ion pair: 446,45
5. Ion pair: acetate
6. Appearance: white amorphous powder without smell
7. Method of synthesis: the peptide is obtained by a classical method of synthesis in a solution by the following scheme:

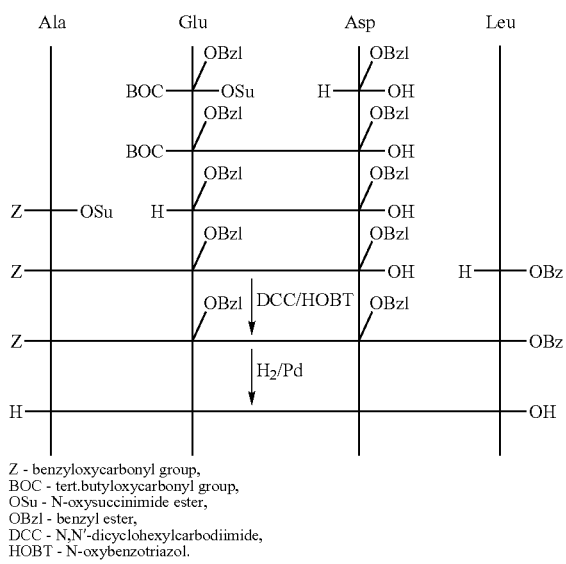

Z - benzyloxycarbonyl group,
BOC - tert.butyloxycarbonyl group,
OSu - N-oxysuccinimide ester,
OBzl - benzyl ester,
DCC - N,N'-dicyclohexylcarbodiimide,
HOBT - N-oxybenzotriazol.

N,N'-dimethylformamide was used as a solvent. When adding aspartic acid, the defense of α-COOH group was applied by salification with triethylamine. BOC-protecting group was removed with trifluoracetic acid (TFA) solution and Z-protecting groups—with catalytic hydrogenation. The product was extracted and purified by the method of preparative high-performance liquid chromatography (HPLC) on a reversed phase column.

8. Properties of the finished product:
   amino acid analysis Glu 1,00; Asp 1,02; Ala 1,00; Leu 1,06;
   peptide content 98,33% (by HPLC, 220 nm);
   thin layer chromatography (TLC)— individual, $R_f$=0,85 (acetonitrile-acetic acid-water 5:1:3);
   moisture content: 7%;
   pH 0,001% solution: 4.40;
   specific rotary power: $[\alpha]_D^{22}$: −42° (c=1, $H_2O$).

Example of Synthesis:

1. BOC-Glu(OBzl)-Asp(OBzl)-OH (I), N-tert. butyloxycarbonyl-(γ-benzyl)-glutamyl-(β-benzyl)aspartate 4.34 g (0.0100 mol) of N-oxysuccinimide ester of N-tert.butyloxycarbonyl-(γ-benzyl)glutamic acid (BOC-Glu(OBzl)-OSu) is dissolved in 20 ml of dimethylformamide and added 1.72 ml (0.0125 mol) of triethylamine and 2.80 g (0.0125 mol) of β-benzyl aspartate. The mixture is stirred for 24 hours at room temperature. Afterwards the product is precipitated with 0.5N sulphuric acid solution (150 ml), extracted by ethyl acetate (3×30 ml), washed in 0.5N sulphuric acid solution (2×20 ml), water, 5% sodium bicarbonate solution (1×20 ml), water, 0.5N sulphuric acid solution (2×20 ml), water. The product is dried over anhydrous $Na_2SO_4$. Ethyl acetate is filtered and removed in vacuo at 40° C., the residue is dried in vacuo over $P_2O_5$. 5.68 g (≈100%) of oil is obtained. $R_f$=0.42 (benzene-acetone 2:1, Sorbfil plates, Silicagel—8-12 μm, development by UV and chlorine/benzidine).

2. TFA-H-Glu(OBzl)-Asp(OBzl)-OH (II), (γ-benzyl) glutamyl-(β-benzyl)aspartate trifluoracetate 5.68 g (,0.01 mol) of N-tert.butyloxycarbonyl-(γ-benzyl)glutamyl-(β-benzyl)aspartate (1) is dissolved in 2 0 ml of dichlormethan-trifluoracetic acid mixture (3:1). Two hours later the solvent is removed in vacuo at 40° C. The removal is repeated with an addition of another portion of dichlormethan (2×10 ml). The residue is dried in vacuo over NaOH. 5.80 g (≈100%) of oil is obtained. $R_f$=0.63 (n-butanol-pyridine-acetic acid-water, 15:10:3:12).

3. Z-Ala-Glu(OBzl)-Asp(OBzl)-OH (III), N-carbobenzyloxyalanyl-(γ-benzyl)-glutamyl-(β-benzyl) aspartate 5.65 g (0.01 mol) of (γ-benzyl)glutamyl-(β-benzyl)aspartate trifluoracetate (II) is dissolved in 10 ml of dimethylformamide, added 2.80 ml (0.02 mol) of triethylamine and 4.14 g (0.013 mol) of N-oxysuccinimide ester of N-carbobenzyloxyalanine. The reacting mixture is stirred for 24 hours at room temperature.

The product is precipitated with 0.5n sulphuric acid solution (150 ml), extracted by ethyl acetate (3×30 ml), washed in 0.5n sulphuric acid solution (2×20 ml), water, 5% sodium bicarbonate solution (1×20 ml), water, 0.5n sulphuric acid solution (2×20 ml), water and dried over anhydrous sodium sulphate. Ethyl acetate is filtered and removed in vacuo at 40° C. The residue is recrystallised in the ethyl acetate/hexane system. The product is filtered and dried in vacuo over $P_2O_5$. The yield is 4.10 g (66%). The temperature of melting ($T_{ml}$) is 154° C. $R_f$=0.48 (benzene-acetone, 1:1), $R_f$=0,72 (n-butanole-pyridine-acetic acid-water, 15:10:3:12).

4. Z-Ala-Glu(OBzl)-Asp(OBzl)-Leu-OBzl (IV), N-carbobenzyloxyalanyl-(γ-benzyl)glutamyl-(β-benzyl)aspartyl-leucine benzyl ester 2.00 g (5 mol) of tosylate of leucine benzyl ester (TosOH H-Leu-Obzl) is suspended in 15 ml of tetrahydrofuran and added 0.7 ml (5 mmol) of triethylamine while stirring. In 5 minutes 2.0 g (3.1 mmol) of N-carbobenzyloxyalanyl-(γ-benzyl)glutamyl-(β-benzyl)aspartate (III) and 0.5 g (3.5 mmol) of N-oxybenzotriazol are added. The mixture is cooled down to 0° C. Afterwards, 0.72 g (3.5 mmol) of N,N'-dicyclohexylcarbodiimide solution cooled down to 0° C. is added in 5 ml of tetrahydrofuran. The mixture is stirred at this temperature for 2 hours and left to blend for a night at room temperature.

The dicyclohexylurea is filtered out, the solvent is dried in vacuo, the residue is suspended in ethyl acetate (30 ml) and the solution is washed consecutively 1 N $H_2SO$ solution, water, 5% $NaHCO_3$ solution, 1 N $H_2SO_4$ solution, water and dried over anhydrous sodium sulphate. The solvent is dried in vacuo and the product is crystallised in the ethyl acetate/hexane system. The yield is 1.50 g (55%), $R_f$=0.62 (benzene-acetone, 2:1).

5. H-Ala-Glu-Asp-Leu (SEQ ID NO:1)-OH (V), alanyl-glutamyl-aspartyl-leucine hydroxide 1.5 g of N-carbobenzyloxyalanyl (γ-benzyl)glutamyl-(β-benzyl)aspartyl-leucine (IV) is hydrogenated in the methanol-water-acetic acid (3:1:1) system over Pd/C catalyst. Completeness of the deblocking reaction is monitored by TLC method in the benzene/acetone (2:1) and acetonitrile-acetic acid-water (5:1:3) systems. On the reaction completion the catalyst is filtered out, the filtrate is removed in vacuo and the residue is recrystallised in the water/methanol system. The product is dried in vacuo over KOH. The yield is 600 μg (79%). $R_f$=0.85 (acetonitrile-acetic acid-water, 5:1:3).

For purification, 540 mg of the product is dissolved in 5 ml of 0.1 trifluoracetic acid and subjected to HPLC on a reversed phase column (50×250 mm, Diasorb-130-$C_{16}$T, 7 μm). The employed chromatograph is Beckman System Gold, 126 Solvent Module, 168 Diode Array Detector Module. The conditions of chromatography A: 0.1% of TFA; B: 50% of MeCN/0.1% of TFA, gradient B 0→50% in 100 minutes. Sample volume constitutes 5 ml, detection is conducted by 215 nm, scanning—by 190-600 nm. The flow rate equals 10 ml/min. The fraction is selected within 62,0-67,0 minutes.

The solvent is removed in vacuo at a temperature not exceeding 40° C. The removal is multiply repeated (5 times) with 10 ml of 10% acetic acid solution.

The residue is finally dissolved in 20 ml of deionised water and lyophilized. 380 mg of purified product in the form of amorphous odourless white powder is obtained.

6. Analysis of the Finished Product

Peptide content is defined by HPLC on Phenomenex LUNA C18 column, 4.6×50 mm. A: 0,1% TFA; B:MeCN/0.1% TFA; grad. B: 0→20% in 5 min., 20%-50% in 15 min. The flow speed equals 1 ml/min. Detection by 220 nm, scanning—by 190-600 nm, the sample volume is 20 μl. Peptide content—98,33%;

Amino acid analysis is carried out on AAA "T-339" Prague tester. Hydrolysis is conducted in 6N HCl at 125° C. for 24 hours. Glu 1,00; Asp 1,02; Ala 1,00; Leu 1,06;

TLC: individual, $R_f$=0.85 (acetonitrile-acetic acid-water, 5:1:3, Sorbfil plates, 8-12 μкм Silicagel, developing in chlorine/benzidine);

Moisture content: 7% (gravimetrically, according to the mass loss by drying 20 mg at 100-C).

pH 0,001% solution: 4,40 (potentiometrically);

Specific rotary power: $[\alpha]_D^{22}$: −42° (c=1, $H_2O$), "Polamat A", Carl Zeiss Jena.

EXAMPLE 2

Effect of the Tetrapeptide on the Functional State of Alveolar Macrophages in Infectious Model of Acute Inflammation in Case of Bacterial Lung Injury in Rats The study was conducted on 120 white mongrel rats with average body weight 200-230 g. The animals were divided at random into 3 groups: 10 (intact), 60 (control) and 50 (experimental). In order to infect the animals there was used twenty-four-hours' culture of Staphilococcus aureus 209, which is tropic to rodents pulmonic tissue. There was also used a cellular suspension 5×$10^6$ cl/ml with Freind adjuvant (25% of total volume). Before infecting the animals were exposed to a supercooling at temperature −20° C. for 1 hour. Then the animals were infected using light thiopental narcosis (8 mg/100g of body weight) in sterile box. Injections of tetrapeptide were started in 2 days after infecting and were conducted for 7 days (daily, intraperitoneally in dose of 0,2 μg/kg). Control animals were administered with 0.9% NaCl solution. The animals were excluded from the trial on the 1, 3, 6, 10, 15 h and $20^{th}$ days by the method of cervical dislocation. In each period there was conducted BAFL testing in order to estimate its cellular content and AM phagocytic activity, superoxid-anion (SA) production and total free radical production by BAFL cells. On the 1 and the $6^{th}$ days of the study there was conducted lung morphological examination.

The obtained results are represented in Tables 1 and 2. Staphylococcus intratracheal administration to the animals led to the development of acute bacterial inflammatory process with morphological dynamics and lethality a bout 20% in the first 48 hours. Control animals reported serous and fibrinous exudant in the alveolar lumen, pronounced edema of perivascular and peribronchial areas, focal and diffuse infiltration of the interalveolar septa by neutrophiles, mucus and neutrophile leukocytes in bronchi lumens. On the morphological level on the $6^{th}$ day of the experiment control animals revealed forming of stable focal infiltrative changes in lung tissue, such as cellular detritus and fibrin accumulations, fibroblast proliferation with signs of interstitial inflammation. Together with inflammatory process there took place significant increase in number of neutrophiles and AM in BAFL, oppression of AM phagocytic activity, pronounced changes of oxidation metabolism.

The obtained results show that under the effect of the tetrapeptide the absolute number of AM in BALF and their functional activity reliably exceed control indices from the $3^{rd}$ till the $10^{th}$ day. Meanwhile, administration of the substance sensibly speeds up the dynamics of BALF cytogram normalization. Thus, by the $6^{th}$ day control group animals reported absence of the pronounced sign of inflammatory reaction, while BALF cytogram indices of control group animals reliably exceeded those of intact animals.

Estimation of the dynamics of SA production in AM response to stimulators of the respiratory explosion there was revealed that tetrapeptide administration reliably increases basal and zymosan-stimulated production of SA. Tetrapeptide administration also led to the more rapid normalization of free radical production of BAFL cells.

Tetrapeptide Ala-Glu-Asp-Leu (SEQ ID NO:1) administration in the dose of 0,2 µg/kg of body weight contributed to speeding-up the processes of lung tissue reparation. Under the effect of this substance there took place earlier coercion of inflammatory reaction, more rapid exudates resorption, and, as a result, accelerated restoration of lung structural integrity as compared to the animals, which were not administered with this tetrapeptide.

EXAMPLE 3

Effect of the Tetrapeptide on Chronic Fibrosis Inflammatory Process (Bleomycine Lung Fibrosis) in Rats The experiment was carried out on 120 white mongrel rats weighing 130-160 g. The animals were divided at random into 3 groups, 40 animals in each. Then the animals were subjected to a thrice-repeated intratracheal administration of bleomycine solution (at a rate of 10.0 mg per kg of body weight) with 2 weeks interval. The tetrapeptide was administered intraperitoneally in the dose of 0,2 µkg/kg of body weight in sterile 0,9% NaCl solution in the course of 7 days beginning from the 5h day after each bleomycine installation.

10 animals of each group were excluded from the experiment by the method of cervical dislocation on the 15, 30, 45 and 60 days after experiment onset.

In each period there was conducted broncho-alveolar lavage fluid (BALF) test in order to estimate its cellular content, and alveolar macrophages phagocytic activity, production of superoxide-anion and total free radical production by BALF cells. In the blood and BALF there were estimated the number of circulating immune complexes (CIC). After the last bleomycin administration there was conducted lung examination.

The results of the experiments are represented in Tables 3 and 4. It is seen from the tables that intratracheal bleomycin installations led to the delay of body weight growth. By the $60^{th}$ day control animals reported a reliable increase of ventricular index up to 66,2±2,3%, caused by the hypertrophy of the right heart ventricle, this evinces hemodynamic changes in lesser circulation and forming of pulmonary heart.

Animals administered with the tetrapeptide reported indices of the body weight with a tendency to increase, but there were no reliable difference between these indices and those of intact animals within all periods of the study. The hypertrophy of the right heart ventricle was considerably less if compared to that of the control animals, the ventricular index increased only to 46,6±1,4%.

After the $3^{rd}$ bleomycine installation by the morphological methods in the lungs there were registered signs of the significant interstitial fibrosis with cysts forming. There was observed a thickening of intralveolar septa due to connective tissue vegetation. The obtained data show that the process that takes place in the lungs, is an interstitial fibrosis accompanied by the disturbance of the organ general architectonics, development of the areas with compensatory emphysema and going on inflammatory process.

Tetrapeptide administration did not utterly prevent the development of sclerosis foci, but lung morphologic changes were reliably less pronounced as compared to control animals. Meanwhile the connective tissue remained more friable and contained smaller number of collagen fibre.

Indices of circulating immune complexes (CIC) content in blood serum and BAFL evidence the tensity of immunopathologic processes under bleomycine lung injury. Against a background of tetrapeptide administration the level of CIC in the blood exceeded the analogues indices in intact animals beginning from the $30^{th}$ day of the process, but they were reliably lower than those in control animals. The level of CIC in BAFL under the effect of was reliably lower of the indices in control animals beginning from $30^{th}$ day of experiment.

The process of fibrosis development was accompanied by significant changes of BAFL cytological content with reliable increase of neutrophile leucocytes and lymphocytes number. Tetrapeptide administration reliably decreased the number of lymphocytes on the $30^{th}$ and $60^{th}$ day as compared to the control animals (1,75±0,45×10$^6$ and 1,11±0,15×10$^6$ cells/lungs as compared to 5,13±0,51×10$^6$ and 4,16±0,45×10$^6$ cells/lungs respectively). Under the effect of the tetrapeptide AM phagocytic activity reliably exceeded the indices of control animals on the $45^{th}$ and $60^{th}$ day of the study (phagocytic index was 75,6±4,5 and 78,6±3,2 as compared to 46,3±2,8 and 57,6±4,8 in control group). The tetrapeptide also contributed to a decrease of basal superoxid-anion production in response to respiratory explosion stimulators.

Thus, Ala-Glu-Asp-Leu tetrapeptide suppressed the inflammatory reaction, which develops in the rat lungs after bleomycine introduction, it was expressed in the decrease of fibrosis changes in lungs, hemodynamic disorders of lesser circulation and myocardial hypertrophy. There was registered the decrease in the level of immune complexes in BAFL and blood, decrease in the number of lymphocytes in BAFL. Under the effect of the substance there increased the number of AM and their functional activity, as well as their absorbing activity. There was registered a decrease in SA basal level and total free-radical production. All these data evince the pharmacologic activity of the tetrapeptide in the dose of 0,2 µg/kg of body weight as a substance, restoring lungs function.

EXAMPLE 4

Effect of the Tetrapeptide on the Lungs in Rats with Sublethal Hyperoxic Injury

The experiment was conducted on 96 white mongrel rats weighing 200-230 g. The animals were divided into three groups: 8 intact animals, 48 control and 40 experimental animals. The animals were exposed to oxygenation by 100% oxygen during 60 hours in the running mode by normal pressure in chamber with oxygen expenditure, providing 8-10 full changes of the gas medium in one hour. Tetrapeptide administration was set out on the $3^{rd}$ day of being in the normal atmosphere. Experimental animals were administered with the tetrapeptide (intraperitoneal administration in the dose of 0,2 µg/kg of body weight, dissolved in 0.9% sodium chloride solution (natural saline), 10 injections, every other day). Morphological study of the lungs was conducted on the 1, 10, 30, 40 and $50^{th}$ day after the experiment onset, eliminating the animals from the trial by the method of cervical dislocation. There were conducted biometrical studies, estimation of BALF cytogram and AM phagocytic activity. BALF cellular content was estimated by coloring of the precipitated cells on the glass following the Leishman-Romanowsky method.

The results of the study are represented in Tables 5 and 6. The data obtained show that after hyperoxic injury control animals reported reliable lap in body mass increase. Meanwhile, an increase of absolute and relative indices of the heart and lungs weight reveal the development of the lingering pathologic process in the lungs with hemodynamic disorders in lesser circulation and compensatory myocardial hypertrophy. In the lungs there was revealed emphysema and peribronchial and perivascular fibrosis. The process of hyperoxic injury development was accompanied by the increase in the absolute number of neutrophiles and lymphocytes in BALF, though the number of macrophages was almost within the norm. There took place a reliable decrease of AM phagocytic activity on the $10^{th}$ and $20^{th}$ day of the process.

The data obtained show that tetrapeptide administration contributed to the decrease of pathomorphological changes manifestation, such as interstitial fibrosis, emerging of atelectasis foci, cellular infiltration and, thus, contributed to a more adequate course of reparative processes in lungs. The values of the lungs and heart weight and deceleration of the body weight growth were less pronounced in the animals of the experimental group as compared to those of the control group. Against a background of tetrapeptide administration by the 10-20 day there was registered a reliable decrease of neutrophiles number as well as an increase of the number and phagocytic activity of AM in BALF. In particular, on the $10^{th}$ and $20^{th}$ day of the study the phagocytic index was 50,8±2,3 and 45,5±2,6 as compared to the indices of control animals (27,3±2,7 and 26,4±2,8 respectively (p<0,05).

Thus, Ala-Glu-Asp-Leu (SEQ ID NO:1) tetrapeptide administration of the in the dose of 0,2 µg/kg of body weight in this model exerted protective effect on lungs morphology and physiologic functions.

EXAMPLE 5

Effect of the Tetrapeptide on the Growth of Lung Organotypical Culture Explants of Mature Rats Lung tissue explants of mature Wistar rats were cultivated in petri dishes with collagen bottom cover. The nutritious medium was composed of 35% Eagle's medium, 35% Hanx solution, 25% calf fetal serum and 5% of chicken embryonic extract with added glucose, insulin, gentamycin and glutamin. Ala-Glu-Asp-Leu (SEQ ID NO:1) tetrapeptide was added into the cultural medium in fixed concentrations, from 0,01 to 20,0 ng per ml of nutritious medium. The same amount of natural saline solution was added to the control explants. After 3 days of incubation at the temperature of 37° C. there was assessed an extension of explants' area using phase contrast microscope. Biological activity of the preparation was evaluated by the change of square index (SI) of the explants cultivated in the medium containing the peptide, compared to the control.

The results of this experiment are displayed in Table 7, which shows, that Ala-Glu-Asp-Leu tetrapeptide reliably stimulates the growth of organotypic lung culture explants in a scope of concentrations from 1,0 to 10,0 ng/ml.

Thus, the administration of Ala-Glu-Asp-Leu (SEQ ID NO:1) tetrapeptide contributes to the accelerated renovation of normal lung tissue cell population.

EXAMPLE 6

Study of the Tetrapeptide for General Toxicity

The general toxic effect of tetrapeptide was studied in compliance with "The manual of Experimental (Pre-Clinical) Study of New Pharmacological Substances" (2000): acute toxicity was studied in conditions of tetrapeptide single administration, subacute and chronic toxicity were investigated in conditions of long tetrapeptide administration.

Acute toxicity was investigated on 60 white mongrel male mice weighing 20-23 g. The animals were randomized to 6 equal groups. They were intramuscularly injected with the tetrapeptide once in the doses of 1 mg/kg, 2 mg/kg, 3 mg/kg, 4 mg/kg, 5 mg/kg in 0.25 ml of natural saline solution. The control animals received the same amount of natural saline solution (0.9%).

Subacute toxicity of the tetrapeptide was investigated on 60 white mongrel male rats weighing 150-250g. The animals of the experimental groups were exposed to intramuscular injection of the tetrapeptide in the doses of 1 µg/kg, 0,1 mg/kg, 1 mg/kg in 0,5 ml of natural saline solution, once a day for 90 days. The animals of the control group were administered with natural saline solution in the same amount. Before the onset of tetrapeptide administration in the $30^{th}$, $60^{th}$ and $90^{th}$ day the animals were exposed to an examination of the morphological composition and characteristics of the peripheral blood. On the completion of the experiment there were studied biochemical and coagulological blood indices.

The tetrapeptide was investigated for chronic toxicity for 6 months, taking into consideration the recommended period of administration, on 100 male guinea-pigs weighing 300-350 g. The animals of the experimental groups were intramuscularly injected with the tetrapeptide in the doses 1 µg/kg, 0,1 mg/kg, 1 mg/kg in 0,5 ml of natural saline solution, once a day for 6 months. The animals of the control group were administered with natural saline solution in the same amount.

These animals were exposed to the assessment of the amount of erythrocytes, hemoglobin, reticulocytes, thrombocytes, leucocytes, leukocytic formula, speed of erythrocytes sedimentation (SES), erythrocytes resistance in peripheral blood. Together with this there was measured the total protein content in the blood serum according to the method of Lowry, potassium and sodium content were measured according to the method of plasma spectrophotometry. On completion of the experiment the animals were subjected to a pathomorphological examination to assess the state of brain and spinal marrow, cerebrospinal ganglia, thyroid gland, adrenal glands, testes, pituitary body, heart, lungs, aorta, liver, kidneys, urinary bladder, pancreas, stomach, small intestine, large intestine, thymus, spleen, lymph nodes, bone marrow.

Study of tetrapeptide acute toxicity revealed that single tetrapeptide injection in the dose, exceeding the therapeutic one 5000 times, recommended for clinical application, does not cause any toxic reactions, this evidences that this substance may be widely adopted in therapeutics.

Studies of subacute and chronic toxicity demonstrate that the tetrapeptide does not reveal any side-effects during long term administration in the doses, 100-1000 times exceeding the therapeutic one.

Study of the tetrapeptide effect on blood morphological content of guinea-pigs revealed an increase in the number of leucocytes in 6 months after the tetrapeptide administration onset (Table 8). Other indices of blood morphological content did not significantly change. There weren't revealed a reliable effect of the tetrapeptide on SES, erythrocytes resistance and biochemical indices of blood serum.

Assessment of the animals' general state, morphological and biochemical indices of their peripheral blood, morphological state of their intrinsic organs, cardiovascular and respiratory systems, liver and kidney functions revealed on pathologic alterations.

Absence of toxic effect allow to recommend the pharmacologic substance containing the tetrapeptide as an active peptide agent for conducting clinical studies.

TABLE 1

| Day of the study | Animal group | Number of animals in the group (n) | BAFL cytogram, ×10⁶ cells/lungs | | |
|---|---|---|---|---|---|
| | | | Macrophages | Neutrophiles | Lymphocytes |
| | Intact | 10 | 11.9 ± 0.98 | 0.25 ± 0.08 | 0.61 ± 0.18 |
| 1 | Control | 8 | 16.1 ± 2.1 | 32.14 ± 4.15* | 4.05 ± 0.53* |
| 3 | Control | 8 | 18.5 ± 1.8* | 11.56 ± 1.95* | 2.45 ± 0.35* |
| | Tetrapeptide | 9 | 29.7 ± 2.8*+ | 6.98 ± 1.48*+ | 1.68 ± 0.16* |
| 6 | Control | 9 | 17.9 ± 1.8* | 1.54 ± 0.27* | 1.58 ± 0.24* |
| | Tetrapeptide | 8 | 24.9 ± 1.2*+ | 0.52 ± 0.18 | 0.86 ± 0.23 |
| 10 | Control | 8 | 13.8 ± 2.1 | 0.85 ± 0.35 | 1.08 ± 0.38 |
| | Tetrapeptide | 9 | 19.2 ± 2.8*+ | 0.31 ± 0.18 | 0.59 ± 0.28 |
| 15 | Control | 7 | 13.8 ± 2.1 | 0.35 ± 0.23 | 1.12 ± 0.29 |
| | Tetrapeptide | 8 | 16.3 ± 2.8 | 0.21 ± 0.16 | 0.79 ± 0.20 |
| 20 | Control | 7 | 12.6 ± 2.5 | 0.23 ± 0.07 | 0.82 ± 0.26 |
| | Tetrapeptide | 9 | 14.6 ± 2.1 | 0.25 ± 0.11 | 0.56 ± 0.17 |

*p < 0.05 as compared to the intact animals index;
+p < 0.05 as compared to the control.

TABLE 2

| Day of the study | Animal groups | n | Phagocytic index | Phagocytic number |
|---|---|---|---|---|
| | Intact | 10 | 37.9 ± 2.7 | 2.97 ± 0.28 |
| 1 | Control | 8 | 60.3 ± 2.8* | 4.52 ± 0.27* |
| 3 | Control | 8 | 35.7 ± 3.2 | 2.87 ± 0.28 |
| | Tetrapeptide | 9 | 52.4 ± 2.9*+ | 5.83 ± 0.37*+ |
| 6 | Control | 9 | 21.3 ± 2.1* | 1.54 ± 0.25 |
| | Tetrapeptide | 8 | 41.5 ± 3.1+ | 4.98 ± 0.28*+ |
| 10 | Control | 8 | 17.3 ± 1.3* | 1.12 ± 0.28* |
| | Tetrapeptide | 9 | 49.2 ± 2.8+ | 2.98 ± 0.32+ |
| 15 | Control | 7 | 45.6 ± 2.8 | 3.25 ± 0.31 |
| | Tetrapeptide | 8 | 55.9 ± 4.2* | 3.74 ± 0.25 |
| 20 | Control | 7 | 42.1 ± 2.8 | 3.56 ± 0.24 |
| | Tetrapeptide | 9 | 49.3 ± 3.6 | 3.68 ± 0.31 |

*p < 0.05 as compared to the intact animals index;
+p < 0.05 as compared to the control.

TABLE 3

| Day of the study | Animal group | Body weight, g | Relative lungs weight, mg/g of body weight | Ventricular index, right ven./left ven. × 100% |
|---|---|---|---|---|
| 15 | Intact | 157.4 ± 6.5 | 6.2 ± 0.5 | 30.8 ± 1.2 |
| | Control | 138.4 ± 8.4 | 13.8 ± 0.6* | 42.3 ± 1.6* |
| | Tetrapeptide | 151.6 ± 5.6 | 11.3 ± 0.6* | 34.2 ± 1.8+ |
| 30 | Intact | 187.4 ± 6.4 | 6.5 ± 0.3 | 31.4 ± 1.5 |
| | Control | 155.3 ± 6.1 | 15.9 ± 0.5* | 46.2 ± 2.0* |
| | Tetrapeptide | 176.8 ± 5.8 | 12.8 ± 0.4* | 37.2 ± 1.5*+ |
| 45 | Intact | 203.4 ± 6.8 | 6.5 ± 0.4 | 32.1 ± 1.6 |
| | Control | 155.4 ± 7.3* | 19.1 ± 0.3* | 54.3 ± 2.3* |
| | Tetrapeptide | 195.3 ± 6.5+ | 11.5 ± 0.3*+ | 42.3 ± 2.1*+ |
| 60 | Intact | 248.7 ± 6.8 | 6.7 ± 0.3 | 32.4 ± 1.5 |
| | Control | 159.6 ± 8.3* | 21.5 ± 0.8* | 66.2 ± 2.3* |
| | Tetrapeptide | 234 ± 9.3+ | 13.4 ± 0.5*+ | 46.6 ± 1.4*+ |

*p < 0.05 as compared to the intact animals index;
+p < 0.05 as compared to the control.

TABLE 4

| | | Blood | | BAFL | |
|---|---|---|---|---|---|
| Day of the study | Animal group | large CIC, units | medium CIC, units | large CIC, units | medium CIC, units |
| 15 | Intact | 40.8 ± 6.7 | 108.6 ± 9.4 | 38.6 ± 3.8 | 52.9 ± 6.4 |
| | Control | 52.6 ± 7.1 | 192.6 ± 12.5* | 48.2 ± 10.2 | 43.7 ± 9.7 |
| | Tetrapeptide | 47.2 ± 12.3 | 113.4 ± 11.6+ | 42.6 ± 13.1 | 37.6 ± 7.6 |
| 30 | Control | 152.8 ± 14.2* | 386 ± 24.6* | 90.1 ± 12.5* | 92.6 ± 7.1* |
| | Tetrapeptide | 85.9 ± 12.3+ | 187.6 ± 20.4*+ | 52.3 ± 8.3*+ | 72.3 ± 8.1*+ |
| 45 | Control | 161.0 ± 12.3* | 318.7 ± 31.5* | 112 ± 24.6* | 116.4 ± 5.2* |
| | Tetrapeptide | 135.2 ± 12.3+ | 208.7 ± 12.5*+ | 76.3 ± 8.3*+ | 79.4 ± 5.4*+ |
| 60 | Control | 115.5 ± 13.5* | 658.4 ± 8.1* | 93.1 ± 12.4* | 83.6 ± 6.8* |
| | Tetrapeptide | 81.3 ± 11.3*+ | 159.4 ± 12.8+ | 53.2 ± 9.4+ | 41.8 ± 6.7+ |

*p < 0.05 as compared to the intact animals index;
+p < 0.05 as compared to the control.

TABLE 5

| Animal group | Body weight, g | Heart weight g | Heart weight mg/g of body weight | Lungs weight g | Lungs weight mg/g of body weight |
|---|---|---|---|---|---|
| Intact | 232 ± 4 | 0.79 ± 0.01 | 3.4 ± 0.4 | 2.00 ± 0.05 | 8.6 ± 0.5 |
| Control | 190 ± 7* | 0.87 ± 0.02 | 4.6 ± 0.5* | 2.43 ± 0.07* | 12.8 ± 0.9* |
| Tetrapeptide | 228 ± 6+ | 0.80 ± 0.02 | 3.5 ± 0.6+ | 2.14 ± 0.06 | 9.4 ± 0.8+ |

*$p < 0.05$ as compared to the intact animals index;
+$p < 0.05$ as compared to the control.

TABLE 6

| Day of the study | Animal group | BAFL cytogram, 106 cells/lungs Macrophages | Neutrophiles | Lymphocytes | Phagocytic activity of AM Phagocytic index | Phagocytic number |
|---|---|---|---|---|---|---|
| 1 | Intact | 12.6 ± 1.2 | 0.53 ± 0.16 | 0.71 ± 0.2 | 37.6 ± 2.1 | 3.08 ± 0.31 |
|   | Control | 16.1 ± 0.9 | 9.84 ± 0.86* | 4.95 ± 0.65* | 51.2 ± 3.2* | 4.75 ± 0.32* |
| 10 | Control | 17.3 ± 1.5 | 4.52 ± 1.02* | 3.01 ± 0.35* | 27.3 ± 2.7* | 2.82 ± 0.36 |
|   | Tetrapeptide | 29.8 ± 2.5*+ | 1.06 ± 0.29*+ | 2.92 ± 0.31* | 50.8 ± 2.3+ | 5.78 ± 0.42*+ |
| 20 | Control | 13.8 ± 2.6 | 3.06 ± 0.75* | 1.45 ± 0.18* | 26.4 ± 2.8* | 1.82 ± 0.23* |
|   | Tetrapeptide | 24.6 ± 2.3*+ | 0.95 ± 0.32+ | 0.83 ± 0.25+ | 45.8 ± 2.6*+ | 3.35 ± 0.35+ |
| 30 | Control | 12.7 ± 1.8 | 2.98 ± 0.41* | 2.04 ± 0.23* | 31.5 ± 3.1 | 2.56 ± 0.24 |
|   | Tetrapeptide | 16.8 ± 2.1 | 0.85 ± 0.23+ | 1.42 ± 0.31* | 42.7 ± 2.5 | 2.83 ± 0.36 |
| 40 | Control | 10.5 ± 1.4 | 2.56 ± 0.3* | 2.64 ± 0.27* | 36.2 ± 2.3 | 3.26 ± 0.25 |
|   | Tetrapeptide | 14.3 ± 1.9 | 0.86 ± 0.21+ | 2.65 ± 0.31* | 40.3 ± 2.3 | 3.45 ± 0.23 |
| 50 | Control | 11.2 ± 2.1 | 2.13 ± 0.45* | 3.21 ± 0.35* | 34.8 ± 3.2 | 3.02 ± 0.25 |
|   | Tetrapeptide | 12.3 ± 1.8 | 0.76 ± 0.14+ | 3.65 ± 0.19* | 38.5 ± 2.3 | 3.21 ± 0.24 |

*$p < 0.05$ as compared to the intact animals index;
+$p < 0.05$ as compared to the control.

TABLE 7

| Index | Tetrapeptide concentration, ng/ml | | | | | | |
|---|---|---|---|---|---|---|---|
|   | 0.01 | 0.1 | 0.5 | 1.0 | 2.0 | 10.0 | 20.0 |
| SI, % compared to the control | 2 | 14 | 9 | 22* | 53* | 25* | 9 |

*$p < 0.05$ as compared to the control.

TABLE 8

| Index | Tetrapeptide administration (1 кГ/кГ) | | | |
|---|---|---|---|---|
|   | 3 months | | 6 months | |
|   | Control (n = 25) | Tetrapeptide (n = 25) | Control (n = 25) | Tetrapeptide (n = 25) |
| Erythrocytic, ×10$^{12}$/l | 5.2 ± 0.4 | 5.1 ± 0.2 | 5.2 ± 0.4 | 5.1 ± 0.3 |
| Hemoglobin, g/l | 13.9 ± 1.2 | 14.2 ± 1.3 | 14.1 ± 0.9 | 14.3 ± 0.8 |
| Reticulocyte, % | 1.22 ± 0.06 | 1.21 ± 0.07 | 1.16 ± 0.07 | 1.21 ± 0.08 |
| Thrombocyte, ×10$^9$/l | 139.5 ± 8.9 | 141.4 ± 8.1 | 145.2 ± 9.1 | 149.3 ± 9.2 |
| Leucocytes, ×10$^9$/l | 9.3 ± 0.7 | 9.5 ± 1.1 | 8.9 ± 0.4 | 11.4 ± 0.4* |
| Relating to stab neuropiles, % | 0.26 ± 0.02 | 0.32 ± 0.07 | 0.41 ± 0.04 | 0.31 ± 0.05 |
| Segmented neutrophiles, % | 44.1 ± 2.4 | 45.6 ± 3.9 | 46.9 ± 4.3 | 41.3 ± 2.80 |
| Eosinopenia, % | 0.60 ± 0.03 | 0.60 ± 0.04 | 0.82 ± 0.05 | 0.54 ± 0.06 |
| Basophil, % | 0.60 ± 0.03 | 0.70 ± 0.05 | 0.75 ± 0.04 | 0.63 ± 0.06 |
| Monocytes, % | 2.70 ± 0.02 | 2.50 ± 0.01 | 2.60 ± 0.03 | 1.80 ± 0.02 |
| Lymphocytes, % | 50.7 ± 2.8 | 51.8 ± 2.6 | 45.4 ± 2.7 | 43.6 ± 2.9 |
| СОЭ, мм/ч | 1.76 ± 0.08 | 1.68 ± 0.06 | 1.95 ± 0.04 | 1.86 ± 0.07 |
| Erythrocytes resistance % | | | | |
| NaCl    maximal | 0.40 ± 0.03 | 0.43 ± 0.04 | 0.41 ± 0.02 | 0.41 ± 0.02 |
|            minimal | 0.33 ± 0.02 | 0.31 ± 0.02 | 0.32 ± 0.03 | 0.29 ± 0.02 |
| Total protein in blood serum, g/l | 71.9 ± 3.6 | 72.3 ± 3.4 | 74.1 ± 3.5 | 72.5 ± 3.7 |

TABLE 8-continued

| | Tetrapeptide administration (1 кГ/кГ) | | | |
| --- | --- | --- | --- | --- |
| | 3 months | | 6 months | |
| Index | Control (n = 25) | Tetrapeptide (n = 25) | Control (n = 25) | Tetrapeptide (n = 25) |
| Sodium content in blood serum, mmol/l | 148.5 ± 6.3 | 149.3 ± 7.2 | 154.2 ± 6.8 | 151.3 ± 5.7 |
| Potasium content in blood serum, mmol/l | 5.2 ± 1.7 | 5.1 ± 2.1 | 5.3 ± 2.3 | 5.1 ± 2.4 |

*P < 0.05 as compared to the control.

The invention claimed is:

1. Tetrapeptide alanyl-glutamyl-aspartyl-leucine of the general formula Ala-Glu-Asp-Leu (SEQ ID NO: 1).

2. A pharmaceutical composition comprising tetrapeptide Ala-Glu-Asp-Leu (SEQ ID NO: 1) and a pharmaceutically acceptable carrier.

3. A method of restoring function of a respiratory organ in a patient with diminished respiratory organ function comprising administering to the patient an effective amount of tetrapeptide Ala-Glu-Asp-Leu (SEQ ID NO: 1).

4. The method of claim 3, wherein the tetrapeptide is administered orally or parenterally.

5. The method of claim 3, wherein the diminished respiratory function is due to acute inflammation of the lung caused by bacterial injury.

6. The method of claim 3, wherein the diminished respiratory function is due to chronic fibrosis inflammatory process.

7. The method of claim 3, wherein the diminished respiratory function is due to hyperoxic injury.

8. The method of claim 3, wherein the tetrapeptide accelerates renovation of normal lung tissue cell population.

* * * * *

```
                        SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Synthetic peptide

<400> SEQUENCE: 1

Ala Glu Asp Leu
1
```